(12) United States Patent
Huszár et al.

(10) Patent No.: US 9,238,636 B2
(45) Date of Patent: Jan. 19, 2016

(54) PROCESS FOR PREPARATION OF DRONEDARONE BY GRIGNARD REACTION

(71) Applicant: SANOFI, Paris (FR)

(72) Inventors: Csaba Huszár, Budapest (HU); Adrienn Hegedus, Budapest (HU); Zsolt Dombrády, Budapest (HU)

(73) Assignee: SANOFI, Paris (FR)

( * ) Notice: Subject to any disclaimer, the term of this patent is extended or adjusted under 35 U.S.C. 154(b) by 0 days.

(21) Appl. No.: 14/403,528

(22) PCT Filed: May 23, 2013

(86) PCT No.: PCT/EP2013/001520
§ 371 (c)(1),
(2) Date: Nov. 24, 2014

(87) PCT Pub. No.: WO2013/178337
PCT Pub. Date: Dec. 5, 2013

(65) Prior Publication Data
US 2015/0274688 A1    Oct. 1, 2015

(30) Foreign Application Priority Data

May 31, 2012 (EP) .................................... 12462010

(51) Int. Cl.
| C07D 307/80 | (2006.01) |
| C07C 233/65 | (2006.01) |
| C07C 231/02 | (2006.01) |
| C07D 307/79 | (2006.01) |

(52) U.S. Cl.
CPC ............ C07D 307/80 (2013.01); C07C 231/02 (2013.01); C07C 233/65 (2013.01); C07D 307/79 (2013.01)

(58) Field of Classification Search
CPC .................................................... C07D 307/80
USPC .......................................................... 549/67
See application file for complete search history.

(56) References Cited

U.S. PATENT DOCUMENTS

| 3,577,441 A | 5/1971 | Kaminsky et al. |
| 3,657,350 A | 4/1972 | Mooradian et al. |
| 3,937,737 A | 2/1976 | Eiglmeier |
| 4,243,405 A | 1/1981 | Balasubramanyan et al. |
| 4,666,931 A | 5/1987 | Ohishi et al. |
| 5,066,803 A | 11/1991 | D'Ambra et al. |
| 5,223,510 A | 6/1993 | Gubin et al. |
| 6,555,697 B1 | 4/2003 | Schlama |
| 6,828,448 B2 | 12/2004 | Fino et al. |
| 6,846,936 B2 | 1/2005 | Biard |
| 6,855,842 B1 | 2/2005 | Schlama et al. |
| 6,949,583 B2 | 9/2005 | Assens et al. |
| 6,984,741 B2 | 1/2006 | Magerlein |
| 7,148,240 B2 | 12/2006 | Assens et al. |
| 7,312,345 B2 | 12/2007 | Gutman et al. |
| 7,517,876 B2 | 4/2009 | Klein et al. |
| 8,143,269 B2 | 3/2012 | Whitten et al. |
| 8,501,971 B2 | 8/2013 | Friesz et al. |
| 8,658,808 B2 | 2/2014 | Kretzschmar et al. |
| 8,658,809 B2 | 2/2014 | Friesz et al. |
| 8,674,121 B2 | 3/2014 | Kretzschmar et al. |
| 8,686,180 B2 | 4/2014 | Bon et al. |
| 8,748,636 B2 | 6/2014 | Bailly et al. |
| 8,796,489 B2 | 8/2014 | Bailly et al. |
| 8,816,103 B2 | 8/2014 | Friesz et al. |
| 8,871,956 B2 | 10/2014 | Bailly et al. |
| 8,884,033 B2 | 11/2014 | Bon et al. |
| 8,889,734 B2 | 11/2014 | Friesz et al. |
| 8,962,869 B2 | 2/2015 | Grimaud et al. |
| 9,024,046 B2 | 5/2015 | Friesz et al. |

(Continued)

FOREIGN PATENT DOCUMENTS

| CN | 101838252 A | 9/2010 |
| CN | 101993427 A | 3/2011 |

(Continued)

OTHER PUBLICATIONS

Cited in the ISR of pct/ep2013/001520.*

(Continued)

*Primary Examiner* — Taofiq A Solola
(74) *Attorney, Agent, or Firm* — Morrison & Foerster LLP

(57) ABSTRACT

The invention relates to a novel process for the preparation of dronedarone (I) and pharmaceutically acceptable salts thereof, which comprises reacting of compound of formula (IV) with compound of formula (VI) in a Grignard reaction, and the obtained product is isolated and, if desired, converted into a pharmaceutically acceptable salt thereof. The invention also relates to some novel intermediary compounds and processes for the preparation thereof.

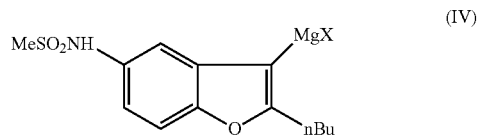

(IV)

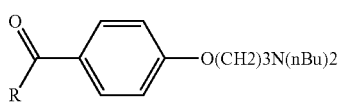

(VI)

17 Claims, No Drawings

(56) References Cited

U.S. PATENT DOCUMENTS

| | | | |
|---|---|---|---|
| 2008/0033209 A1 | 2/2008 | Szarvas et al. |
| 2010/0273764 A1 | 10/2010 | Andrews et al. |
| 2013/0023678 A1 | 1/2013 | Priem et al. |
| 2013/0109868 A1 | 5/2013 | Friesz |
| 2013/0289287 A1 | 10/2013 | Vishnu Newadkar et al. |
| 2014/0018553 A1 | 1/2014 | Grimaud et al. |
| 2014/0081035 A1 | 3/2014 | Friesz et al. |
| 2014/0114081 A1 | 4/2014 | Friesz et al. |
| 2015/0005515 A1 | 1/2015 | Friesz et al. |
| 2015/0018568 A1 | 1/2015 | Friesz |
| 2015/0031901 A1 | 1/2015 | Bon et al. |
| 2015/0031902 A1 | 1/2015 | Huszar et al. |

FOREIGN PATENT DOCUMENTS

| | | | |
|---|---|---|---|
| EP | 0 471 609 A1 | 2/1992 |
| EP | 0 735 083 A1 | 10/1996 |
| FR | 2 833 259 A1 | 6/2003 |
| WO | WO-96/05190 A1 | 2/1996 |
| WO | WO02/48078 | * | 6/2002 |
| WO | WO-02/48078 A1 | 6/2002 |
| WO | WO02/48132 | * | 6/2002 |
| WO | WO-02/48132 A1 | 6/2002 |
| WO | WO-03/040120 A1 | 5/2003 |
| WO | WO-2005/012301 A1 | 2/2005 |
| WO | WO-2007/022501 A2 | 2/2007 |
| WO | WO-2007/022501 A3 | 2/2007 |
| WO | WO-2007/100295 A1 | 9/2007 |
| WO | WO-2007/133637 A2 | 11/2007 |
| WO | WO-2007/133637 A3 | 11/2007 |
| WO | WO-2007/140989 A2 | 12/2007 |
| WO | WO-2007/140989 A3 | 12/2007 |
| WO | WO-2009/044143 A2 | 4/2009 |
| WO | WO-2009/044143 A3 | 4/2009 |
| WO | WO-2010/038029 A1 | 4/2010 |
| WO | WO-2010/040261 A1 | 4/2010 |
| WO | WO-2010/116140 A1 | 10/2010 |
| WO | WO-2010/136500 A1 | 12/2010 |
| WO | WO-2010/136502 A1 | 12/2010 |
| WO | WO-2011/070380 A1 | 6/2011 |
| WO | WO-2011/099010 A1 | 8/2011 |
| WO | WO-2011/104591 A1 | 9/2011 |
| WO | WO-2011/107705 A1 | 9/2011 |
| WO | WO-2011/158050 A1 | 12/2011 |
| WO | WO-2012/004658 A2 | 1/2012 |
| WO | WO-2012/004658 A3 | 1/2012 |
| WO | WO-2012/010788 A1 | 1/2012 |
| WO | WO-2012/010802 A1 | 1/2012 |
| WO | WO-2012/010913 A1 | 1/2012 |
| WO | WO-2012/032545 A1 | 3/2012 |
| WO | WO-2012/127173 A1 | 9/2012 |
| WO | WO-2012/131408 A1 | 10/2012 |
| WO | WO-2012/131409 A1 | 10/2012 |
| WO | WO-2012/131410 A1 | 10/2012 |
| WO | WO-2013/014478 A1 | 1/2013 |
| WO | WO-2013/014479 A1 | 1/2013 |
| WO | WO-2013/014480 A1 | 1/2013 |
| WO | WO-03/048144 A2 | 6/2013 |
| WO | WO-03/048144 A3 | 6/2013 |
| WO | WO-2013/121234 A1 | 8/2013 |
| WO | WO-2013/121235 A2 | 8/2013 |
| WO | WO-2013/121235 A3 | 8/2013 |
| WO | WO-2013/128294 A2 | 9/2013 |
| WO | WO-2013/128294 A3 | 9/2013 |
| WO | WO-2013/128294 A8 | 9/2013 |

OTHER PUBLICATIONS

Abramenko et al. (1975). "Polymethine Dyes—Furo[2,3-g]Benzothiazole Derivatives," Chemistry of Heterocyclic Compounds 11:1361-1364.

Adams et al. (1951). "Quinone imides. IV. P-Quinone Monosulfonimides," Journal of the American Chemical Society 73:1145-1149.

Adams et al. (1956). "Quinone Imides. XXXIX. Adducts of Quinone Monoimides and Conversion of Active Methylene Adducts to Benzofurans," J. Am. Chem. Soc. 78(3):658-663.

Alcaraz et al. (2004). "Novel N-Aryl and N-Heteroaryl Sulfamide Synthesis via Palladium Cross Coupling," Organic Letters 6(16):2705-2708.

Ando et al. (1982). "Motion at the Active Site of Tosylchymotrypsin," Journal of the American Chemical Society 104(11):3172-3178.

Anjanappa et al. (2008). "2-(Trimethylsilyl)ethanesulfonyl Amide as a New Ammonia Equivalent for Palladium-Catalyzed Amination of Aryl Halides," Tetrahedron Letters 49:45854587.

Bartoli et al. (1991). "Unexpected Elimination to a,6-Alkynylketones in the Reaction of Dianions of 1-Arylenaminones with Trimethylchlorosilane," Tetrahedron Letters 32(48):70917092.

Batra et al. (2001). "Syntheses and Biological Evaluation of Alkanediamines as Antioxidant and Hypolipidemic Agents," Bioorganic & Medicinal Chemistry 9(12):3093-3099.

Bavin (1973). "2-Aminofluorene," Org. Syn. Coll. 5:30.

Berthold et al. (2002). "Transfer Hydrogenation in Ionic Liquids Under Microwave Irradiation," Syn. 1607-1610.

Boovanahalli et al. (2004). "Application of Ionic Liquid Halide Nucleophilicity for the Cleavage of Ethers: a Green Protocol for the Regeneration of Phenols from Ethers," Journal of Organic Chemistry 69:3340-3344.

Bourgery et al. (1981). "Synthesis and Antiarrhythmic Activity of New Benzofuran Derivatives," Journal of Medicinal Chemistry 24(2):159-167.

Burton et al. (2003). "Palladium-Catalyzed Intermolecular Coupling of Aryl Chlorides and Sulfonamides under Microwave Irradiation," Organic Letters 5(23):4373-4376.

Castellino et al. (1984). "Synthesis of Benzofurans from Oxygenated Phenoxyamines," Journal of Organic Chemistry 49:4399-4404.

Chauhan et al. (2004). "Microwave Assisted Dealkylation of Alkyl Aryl Ethers in Ionic Liquids," Journal of Chemical Research, pp. 693-694.

Cheng et al. (2007). "Facile Cleavage of Ethers in Ionic Liquid," Bulletin of the Chemical Society of Japan 80(10):2008-2010.

Database PubChem Compound [Online] (Oct. 25, 2006),"CID 10095002—Compound Summary:N-[3-[4-(3-aminopropoxy)benzoyl)-2-butyl-1-benzofuran-5-yl", XP002676507, Database accession No. 15082344. Retrieved from the Internet: URL:http://pubchem.ncbi.nlm.nih.gov/summary/summary.cgi?sid=15082344&viewopt=PubChem [retrieved on May 5, 2012].

Delahay et al. (2007). "Past and Recent Approaches of Preparing Fe-ZSM-5," Current Topics in Catalysis 6:19-33.

Douglass (1959). "Some New Reactions of Methanesulfenyl Chloride," Journal of Organic Chemistry 24:2004-2006.

Denmark et al. (2008). "Lewis Base Catalysis in Organic Synthesis," Angew. Chem. Int. Ed. 47(9):1560-1638.

Fennel (1958). "Quinoline Analogs of Podophyllotoxin. I. Preliminary Experiments. Syntheses of Some 4-Phenylquinoline Derivatives," J. Org. Chem. 23:432-434.

Fieser et al. (1967). "Reagents for Organic Synthesis," John Wiley & Sons, pp. 703-705.

Fontana (2008). "Syntheses of (R,S)-Naproxen and its 6-O-Desmethyiated Metabolite labelled with 2H," J. Labelled Compounds and Radiopharma. 51:239-241.

Gilow et al. (Jun.-Jul. 1991). "Sulfenylation of Some Pyrroles and Indoles," J. Het. Chem. 28:1025-1034.

Groves (1972). "The Friedel—Crafts Acylation of Alkenes," Chem. Soc. Rev. 1:73-97.

Gutowski et al, (2005). "Prediction of the Formation and Stabilities of Energetic Salts and Ionic Liquids Based on ab Initio Electronic Structure Calculations," The Journal of Physical Chemistry B 109:23196-23208.

Haddadin et al. (1976). "Reaction to Benzofurazan Oxide with Unsymmetrical 1, 3-Diketones: Steric Polar Effects," Tetrahedron 32:719-724.

Hauser et al. (1948) "Alkaline Cleavage of Unsymmetrical 6-Diketones. Ring Opening of Acylcyclohexanones to Form c-Acylcaproic Acids," Journal of the American Chemical Society 70:4023-4026.

(56) References Cited

OTHER PUBLICATIONS

Headley et al. (2006). "Dynamic Solvation in Imidazolium-Based Ionic Liquids on Short Time Scales," *Journal of Physical Chemistry* 110:9549-9554.
Horton et al. (1967). "Reactions With Reactive Alkyl Halides," *J. Meth. In Enzymology* 11:556-565.
Ikawa et al. (2007). "Pd-Catalyzed Amidations of Aryl Chlorides Using Monodentate Biaryl Phosphine Ligands: A Kinetic, Computational, and Synthetic Investigation," *Journal of the American Chemical Society* 129:13001-13007.
Imori et al. (2006). "Efficient Demethylation of N,N-Dimethylanilines with Phenyl Chloroformate in Ionic Liquids," *Synlett*. 16:2629-2632.
International Search Report mailed on Jun. 25, 2013, for PCT Patent Application No. PCT/EP2013/001520, filed on May 23, 2013, three pages.
Johnson Matthey Handbook of Pharmaceutical Catalysis, 2009, pp. 1-106.
Joshi et al. (1986). "Some New Fluorinated 6-Ketoamines and Their Copper Complexes," *Synth. React. Inorg. Met. -Org. Chem.* 16(7):1009-1024.
Krongauz et al. (1986). Poly(anilophenylquinoxaline)s. Inst. Elementoorg. Soedin. 28(4):771 (Abstract).
Kurti et al. (2005). Strategic Applications of Named Reactions in Organic Synthesis. El Sevior, pp. 448-449.
Kwiatkowski et al. (1978). "Metal Benzoylpivaloylmethanates, Part I. Free Ligands and Copper(II) Chelates," *Transition Met. Chem.* 3:305-308.
Laszlo et al. (1987). "Catalysis of Friedel-Crafts Alkylation by a Montmorillonite Doped with Transition-Metal Cations," Helvetica Chimica Acta 70:577-586.
Liu et al. (2004). "Cleavage of Methyl Ethers of Flavones by Chloroaluminate Ionic Liquid," *Synthetic Communications* 34:3209-3218.
Majdik (1985). "Studiul reactiei de ciclizare a orto-hidroxibenzilfenilcetonelor in benzofuran derivati," *Revista de Chimie* 36(8):760-761 (with English Translation).
Majdik et al. (1989). "Prepararea unor 2-(aril)-nitrobenzofurani din 0-(nitrofeni1)-acetofenonoxime," *Revista de Chemie* vol. 40, No. 8, pp. 689-693 (with English Translation).
Majdik et al. (1989). "0-Arilarea cetoximelor cu nitroclorbenzeni," *Revista de Chemie* vol. 40, No. 6, pp. 490-493 (with English Translation).
March (Jul. 1, 1992). "Aromatic Electrophilic Substitution," Chapter 11 in *Advanced Organic Chemistry, Reactions, Mechanism and Structure*, 4th edition, Wiley Interscience, pp. 538-542.
March (Jul. 1, 1992). "Aliphatic Nucleophilic Substitution," Part 2 in *Advanced Organic.Chemistry, Reactions, Mechanism and Structure*, 4th edition, Wiley Interscience, pp. 442.
Marvel et al. (1941). "Diphenylacetic Acid," *Org. Synth. Coll.* vol. 1, 224-225.
Mehrotra et al. (2001). "Search for New Chemical Entities as Menses Inducing Agents," Contraception 64:187-191.
Munch et al. (1946). "The Preparation of Some a-Dialkylamino-w-Methylaminoalkanes," *J. Am. Chem. Soc.* 68:1297-1299.
Nagy et al. (2007). "Isomorphous Substitution in Zeolites," Mol. Sieves 5:365-478.
Nakamura et al. (2004). "Pyrazole Derivatives as New Potent and Selective 20-Hydroxy5,6,11,14-Eicosatetraenoic Acid Synthase Inhibitors," Bioorganic Medic. Chem. 12:6209-6219.
Pal et al. (2007). "Synthesis of Monohydroxy-Functionalized Triphenylene Discotics: Green Chemistry Approach," Tetrahedron 63:6874-6878.
Roshchin et al. (1998). "Synthesis of Benzofurans via Pd2+-Catalyzed Oxidative Cyclization of 2-Allylphenols," *Journal of Organometallic Chemistry* 560(1-2):163-167.

Sanfilippo (1988). "Synthesis of (Aryloxy)Alkylamines. 1. Novel Antisecretory Agents with H+K+-ATPase Inhibitory Activity," *J. Med. Chem.* 31(9):1778-1785.
Serajuddin (2007). "Salt Formation to Improve Drug Solubility," Advanced Drug Delivery Reviews 59:603-616.
Shridhar (1981). "Synthesis & Biological Activity of Some New 2-[(5-Nitro-2-Furyl- & 5- Nitro-2-Thienyl)vinyI]-N-Arylsulphonamides & 1-[2-(5-Nitro-2-Furyl & 5-Nitro-2-Thienyl)vinyl]sulphonyl Heterocycles," Indian Journal of Chemistry 208:234-237.
Skeels et al. (1989). "Zeolite Chemistry, Substitution of Iron or Titanium for Aluminum in Zeolites Via Reaction with the Respective Ammonium Fluoride Salts," Acs Symposium series, zeolite Synthesis 398:420-435.
Slusarska et al. (Feb. 1981). "One-Pot Phase-Transfer-Catalysed N-Alkylation of Diphenylphosphinamide with Alcohols in the Presence of Methanesulfonyl Chloride," Synthesis 155-156.
Son et al. (1989). "Stereochemical Mechanism of Iodoacetic Acid Mediated Decomposition of L-Methionine to L-Homoserine Lactone," Journal of the American Chemical Society 11 1(4):1363-1367.
Sun et al. (2004). "N-{2[2-( 4-Phenylbutyl)Benzofuran-4-yl]Cyclopropylmethyl}-Acetamide: An Orally Bioavailable Melatonin Receptor Agonist," *Bioorganic & Medicinal Chemistry Letters* 14:5157-5160.
Tanaka (1967). "Studies on 5-Aminosalicylaldehyde Derivatives. II. Reduction of 5-(p-Sulfophenylazo)Salicylaldehyde Through Poly(5-Nitrilosalicylidene) to 5-Aminosalicylaldehyde Derivatives," *Bulletin of the Chemical Society of Japan* 40(7):1724-1726.
Thornber (1979). "Isosterism and Molecular Modification in Drug Design." *Chem. Soc. Rev.* 8:563-580.
Upthagrove et al. (Nov. 2001). "Importance of Amine $pK_a$ and Distribution Coefficient in the Metabolism of Fluorinated Propranolol Derivatives. Preparation, Identification of Metabolite Regioisomers, and Metabolism by CYP2D6," *Drug Metab. Dispos.* 29(11):1377-1388.
Wamser et al. (1989). "Kinetics and Mechanisms for the Two-Phase Reaction Between Aqueous Aniline and Benzoyl Chloride in Chloroform, with and without Pyridine Catalysis," *J. Org. Chem.* 54:150-154.
Weissman et al. (2005). "Recent Advances in Ether Dealkylation," *Tetrahedron* 61:78337863.
Weitkamp et al. (1986). "Isomorphe Substitution in Zeolithen: Katalyse an Boro-, Alumo-und Galio-Silicaten mit ZSM-5-Strukter," *Chem. Ing. Tech.* 58(12):969-971 (with English Translation).
Wikipedia. (Nov. 5, 2012). "Reduction of Nitro Compounds.".
Wu et al. (2004). "Immobilization of HX: [Hmim]X as Halogenating Agent, Recyclable Catalyst and Medium for Conversion of Alcohols to alkyl halides," *Chinese J. Chem.* 22:619-621.
Wuts (2006). Greene's Protective Groups in Organic Synthesis, Fourth Edition, John Wiley and Sons, Chapter 7, Protection for the Amino Group, pp. 696-926.
Yang et al. (2009). "Structure-Based Virtual Screening for Identification of Novel 11 β-HSD1 Inhibitors," *European J. of Medicinal Chem.* 44(3):1167-1171.
Yin et al. (2000). "Palladium-Catalyzed Intermolecular Coupling of Aryl Halides and Amides," Organic Letters 2(8):1101-1104.
Yin et al. (2002). "Pd-Catalyzed Intermolecular Amidation of Aryl Halides: The Discovery that Xantphos Can Be Trans-Chelating in a Palladium Complex," *Journal of the American Chemical Society* 124:6043-6048.
Zasshi (1956). "Studies on the Syntheses of Phenothiazine Derivatives. I. Syntheses of N-Substituted Phenothiazines by Tosylates," *J. Pharm. Soc. of Japan* 76:637-640 (with English Translation).
U.S. Appl. No. 14/377,484, filed Aug. 7, 2014, by Huszar et al.

\* cited by examiner

PROCESS FOR PREPARATION OF DRONEDARONE BY GRIGNARD REACTION

CROSS-REFERENCE TO RELATED APPLICATIONS

This application is a National Phase application under 35 U.S.C. §371 of International Application No. PCT/EP2013/001520 filed May 23, 2013 and claims the benefit of EP Application No. 12462010.5 filed May 31, 2012, the disclosures of which are incorporated herein by reference in their entirety.

FIELD OF THE INVENTION

The invention relates to a novel process for the preparation of dronedarone and pharmaceutically acceptable salts thereof, to novel intermediary compounds used in this process and their preparation.

TECHNICAL BACKGROUND

Dronedarone, i.e. N-[2-n-butyl-3-[4-[3-(di-n-butylamino)propoxy]benzoyl]-1-benzofuran-5-yl]-methanesulfonamide, having the formula (I):

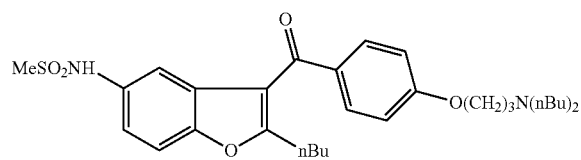

is a known drug for the treatment of arrhythmia (EP0471609).

There are some known processes for the preparation of dronedarone as follows:

In EP 0471609 the following scheme is disclosed for the preparation of dronedarone [Process A]

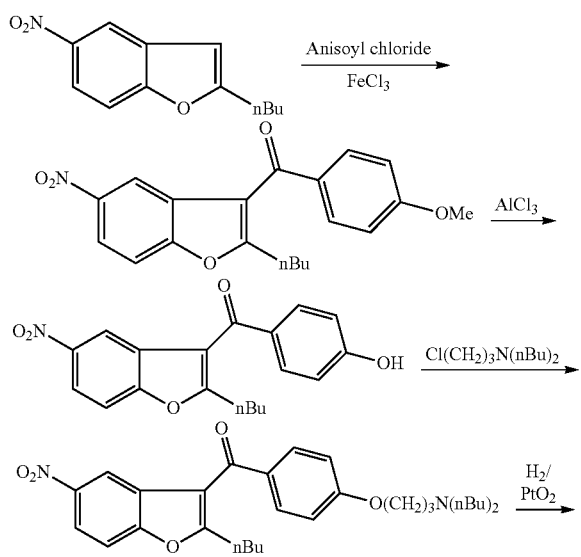

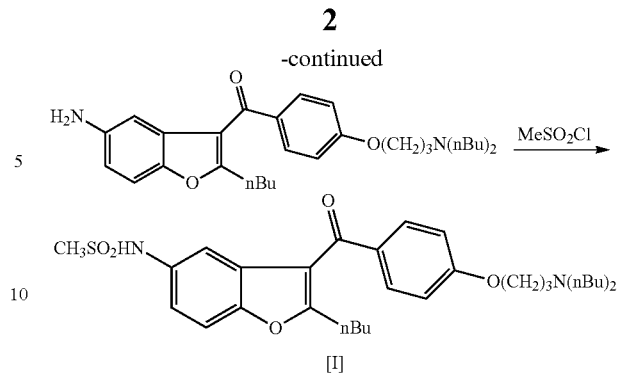

The above mentioned patent description discloses some new intermediary compounds, too.

In WO 02/48078 the following scheme is disclosed for the preparation of dronedarone [Process B]:

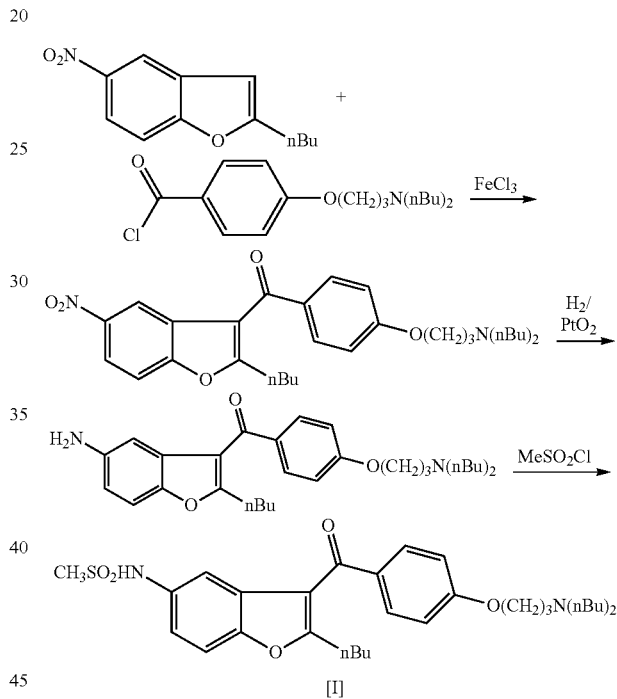

The novelty of the process is based on the adaptation of the Friedel-Crafts reaction in the first step. The process and the intermediary compounds used for the preparation of the benzoylchloride compound of the first step are also disclosed in this document. The further steps of the process are identical with the final steps of the synthetic route disclosed in EP 0471609 [Process A], but in the claims the whole synthetic route is claimed, up to dronedarone.

In WO 02/48132 (Sanofi) the following reaction route is disclosed [Process C]. This method is the so called superconvergent route. In the first step of it 5-amino-2-butyl-benzofuran

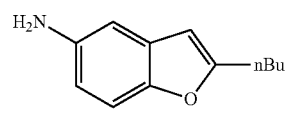

is mesylated and the obtained 2-butyl-5-methanesulfona-
  mido-benzofuran (in HCl salt form) is further reacted in
  the next step as follows:

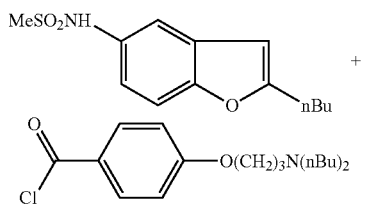

In this process the order of reaction steps are altered, the reduction and the methansulfonylation steps are performed at the beginning part of the procedure. Besides the reaction route for preparation of dronedarone, the starting material 2-butyl-5-methansulfonamido-benzofuran and its preparation are also claimed.

From among the mentioned procedures the first one [Process A] is the so called linear synthesis. In this way of procedure the different parts of the dronedarone are stepwise built up on the starting compound. This method is the least economical because the continuous step by step building of the chemical groups is performed on more and more complicated and expensive molecules, which raises the costs of the preparation.

Furthermore it comprises complicated and harmful reaction steps because aluminium chloride is used in the cleaving reaction of the methoxy group which makes the industrial feasibility more complicated.

In WO 02/48078 (Process B) a shorter synthetic route is disclosed which makes this process more economical, but its last reaction step remained the methansulfonylation reaction of the amino group. This reaction step (see the method described in example 6 of of WO 02/48078) is complicated and gives a low yield of only 61.6%. Pure product can be expected after purification using chromatographic column purification, which method is necessary because of the separation difficulties of the bis-methanesulfonylated product.

The process disclosed in WO 02/48132 (process C) is simpler and more economical taking into consideration the number of the reaction steps. Unfortunately, in the last reaction step rather impure dronedarone.HCl (hydrochloride salt) is formed which is the obvious consequence of the presence of the dibutylamino group in the Friedel-Crafts reaction. According to Examples 3 and 4, the crude dronedarone hydrochloride salt is prepared with a yield of 90% which is further purified and finally the crude dronedarone base is produced with a yield of 86%. This base is reacted with hydrogen chloride gas dissolved in isopropanol which results in pure dronedarone hydrochloride salt. No yield is given for this reaction step. According to example 5 crude dronedarone hydrochloride salt is prepared with a yield of 90%, which is washed with water and reacted with hydrogen chloride gas dissolved in isopropanol, resulting dronedarone hydrochloride salt again. The quality of this product is not known. However, since neither the components used in the Friedel-Crafts reaction nor the resulting products and by-products are soluble in water, the washing step with water cannot result any purification apart from the removal of inorganic salts.

There is another drawback of this process, namely, a dimesylated side-product is formed in the mesylation reaction of the 5-amino-2-butyl-benzofuran. The purification is carried out by crystallization which has a yield of 78.5%.

It is an object of the present invention to provide a novel process for the preparation of dronedarone (I), starting from known and commercially available materials, applying simple, environmentally compatible reagents and solvents, to afford high overall yields and good purity of the product.

SUMMARY OF THE INVENTION

The main aspect of the invention is a process for preparation of dronedarone (I) and pharmaceutically acceptable salts thereof

[I]

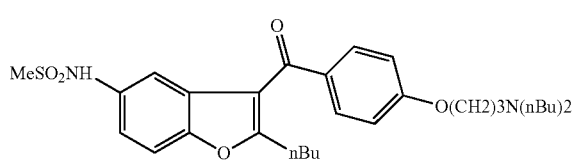

which comprises reacting of compound of formula (IV)

[IV]

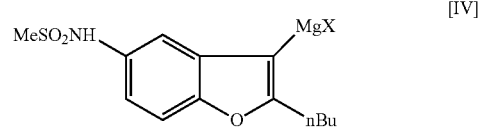

with compound of formula (VI)

[VI]

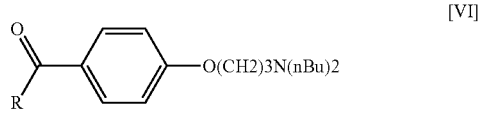

in a Grignard reaction,
isolating the obtained product as a base and, if desired converting it into a pharmaceutically acceptable salt.

The idea of the process is based on the superconvergent synthesis of dronedarone (I) (WO Patent No. 02/48132), but compounds (II) and (V) are coupled with a Grignard reaction. The process is simple, its advantage compared to the previously mentioned [A] and [B] processes is that the Friedel-Crafts acylation of 2-butyl-5-nitrobenzofuran can be avoided.

Further aspects of the invention include the compounds of formula (III), (IV) and (VI) as a new compounds, and processes for the preparation thereof (see below in the "Detailed description of the invention" part).

DETAILED DESCRIPTION OF THE INVENTION

Therefore the present invention relates to a process for the preparation of dronedarone and pharmaceutically acceptable salts thereof. The whole process—starting from compounds available from commercial sources—reads as follows:

(a) a compound of formula (II) (N-(2-butyl-1-benzofuran-5-yl)methanesulfonamide) is halogenated to obtain a compound of formula (III):

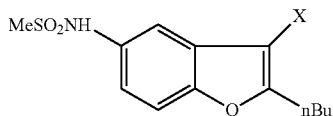

[III]

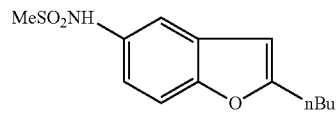

[II]

wherein X is Cl or Br;
(b) the compound of formula (III) obtained in step (a) above is converted by reacting with Mg into a compound of formula (IV):

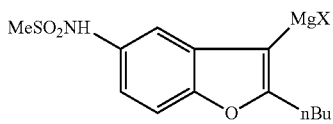

[IV]

wherein X is Cl or Br; compound (IV) is not isolated in the process;
(c) a compound of formula (V) (4-(3-dibutylaminopropoxyl)benzoyl chloride) is reacted with an amine of formula R—H or its salt to obtain a compound of formula (VI):

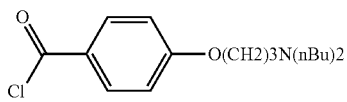

[V]

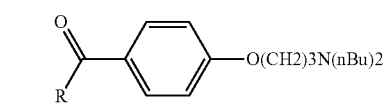

[VI]

wherein R is a group of formula —NR$^1$R$^2$, wherein R$^1$ and R$^2$ are independently selected from H, alkyl, alkyloxy and aryl;
(d) the compound of formula (IV) is reacted with a compound of formula (VI) in a Grignard reaction to obtain dronedarone (I),
and the obtained product is isolated and, if desired, converted into a pharmaceutically acceptable salt thereof.

The intermediates (III), (IV) and (VI) are new compounds, intermediates (III) and (VI) are isolated in stable, pure form. The Grignard reagent of formula (IV), wherein X is Cl or Br, is preparable by reacting a compound of formula (III), wherein X is Cl or Br, with Mg in an anhydrous solvent. As the Grignard reagent is rather sensitive to moisture and oxygen, it is typically not isolated. It is used in the form of an anhydrous, typically ethereal solution.

Said compounds and their preparation processes [i.e. the above steps (a), (b) and (c)] form further objects of the invention.

Compounds of formula (II) and (V) are known from WO 02/48132 (Sanofi).

The reaction of step (a) is typically carried out in a solvent or in a mixture of solvents. The solvent in this step is typically selected from the group of nitriles, ketones or chlorinated solvents and any mixtures thereof. Specific examples include, among others, the mixture of dichloromethane and acetonirtile.

Either organic or inorganic halogenating agents may be used in the halogenations reaction. Typical reagents are N-bromosuccinimide, N-chlorosuccinimide or phosphoroxychloride.

The reaction is typically carried out under cooling, the temperature is typically between −10 and 0° C.

In step (b) the compound of formula (III) is converted to a compound of formula (IV), i.e. to a so-called Grignard reagent by a reaction with Mg. Typically Mg turnings are used.

The reaction is carried out in an anhydrous solvent, typically in ethers, e.g. in tetrahydrofurane (THF), 2- or 3-methyltetrahydrofurane (MeTHF), 1,4-dioxane or diethyl-ether. Usually THF is used. The reaction is typically carried out at an elevated temperature, e.g. under reflux.

The Grinard reagent of formula (IV) is not isolated, it is used in the form of the obtained solution in the Grignard reaction of step (d).

In step (c) a compound of formula (V) is reacted with an amine or a salt thereof. The amine is ammonia or an alkyl, alkyloxy or aryl amine as defined above. Specific examples are ammonia (in form of aqueous solution), dimethylamine HCl, diethylamine, aniline and N,O-dimethyl hydroxylamine HCl.

The reaction in step (c) is typically carried out in a solvent, such as halogenated, especially chlorinated solvents and aliphatic hydrocarbons. Specific examples are dichloromethane, chloroform or n-hexane.

In this step a catalyst, usually a base is used. Specific examples are pyrimidine, K$_2$CO$_3$ and trimethylsilyl chloride (TMSCl).

Due to the fast chemical reaction cooling of the reaction mixture may be beneficial before adding the catalyst. Afterwards, the reaction is usually carried out at a higher temperature, typically between room temperature and reflux temperature.

Step (d) is a Grignard reaction. Suitable reaction conditions are well known in the art (for a review see e.g. Smith, M. B.; March, J. March's Advanced Organic Chemistry, (6th ed.) Wiley, NY, 2007, and references cited therein).

The reaction is carried out in an anhydrous solvent, typically in ethers, e.g. in THF, MeTHF, 1,4-dioxane or diethylether. Usually THF is used.

The reaction is typically carried out in an oxygen-free environment, e.g. under nitrogen or argon atmosphere.

In order to facilitate the reaction a catalyst, such as FeCl$_3$, NiCl$_2$, LiCl, CuCl$_2$ or iron or lithium complex catalysts may be used. A typical catalyst is FeCl$_3$.

In this reaction the temperature is chosen according to the general practice of a person skilled in organic chemistry. Typically the temperature is between 0° C. and reflux temperature, especially room temperature between 15 and 25° C.

Applicable temperature values for each step can be found in the examples.

Each reaction step is generally carried out under atmospheric pressure.

In the processes for the preparation of the intermediary compounds of formula (III) and (VI) the product is typically isolated as a base. If desired, the isolated base can be converted into a salt (acid addition salt) thereof, which is typically a pharmaceutically acceptable salt (possible acids are mentioned below). Theoretically the acid addition salt can be prepared directly if the relating acid is in the final reaction mixture from which the solid product is made (however, this way is not applied in case of these compounds where the base type form has practical importance).

The applicable acid for the preparation of pharmaceutically acceptable salts can be any inorganic or organic acid which forms an acid addition salt with the compound of general formula (I) and (VI). Exemplary acids which can form an acid addition salt are as follows: acetic acid, adipic acid, alginic acid, ascorbic acid, aspartic acid, benzoic acid, benzenesulfonic acid, boric acid, butyric acid, citric acid, ethanesulfonic acid, fumaric acid, hydrogen chloride, hydrogen bromide, hydrogen iodide, 2-hydroxyethanesulfonic acid, maleic acid, oxalic acid, methanesulfonic acid, nitric acid, salicylic acid, tartaric acid, sulfuric acid (forming sulfate or bisulfate anion), sulfonic acid (such as those mentioned herein), succinic acid, toluenesulfonic acid and the like. The hydrogen halogenide salts are typical, especially the hydrogen chloride salt.

Here it is mentioned that on the mesylate group of compounds of general formula (I) and (III) (see the "left side" of the molecules) a salt formation can be carried out (on the amide part of it) by a strong base, e.g. an alkaline hydroxide, typically by sodium hydroxide. However, these salts have less practical importance, but they are within the scope of salts. It means that the phrase "salts" embraces both the acid addition salts and the salts formed by bases (basic salts) in case of compounds of formula (I).

As used herein, the term alkyl includes straight or branched aliphatic hydrocarbon chains of 1 to 6 carbon atoms, e.g., methyl, ethyl, isopropyl and t-butyl.

As used herein, the term "alkoxy" includes alkyl-O— groups. Non-limiting examples of suitable alkoxy groups include methoxy, ethoxy, n-propoxy, isopropoxy and n-butoxy.

As used herein, the term "aryl" includes aromatic monocyclic or polycyclic ring systems comprising 6 to about 14 carbon atoms, preferably 6 to about 10 carbon atoms. Non-limiting examples of suitable aryl groups include phenyl and naphthyl.

The following non-limiting examples further illustrate the invention.

In the examples the following HPLC method was applied for the determination of the purity of the reaction products:
Column: Waters Symmetry C18 4.6×150 mm, 5 μm
Mobile phases:
Mobile phase A: 5 mM sodium phosphate buffer, pH=2.2
Mobile phase B: acetonitrile
Mobile phase C: methanol
Column temp: 25° C.
Auto sampler temp: 20° C.
Gradient:

| Time (min) | A (%) | B (%) | C (%) |
|---|---|---|---|
| 0 | 65 | 30 | 5 |
| 20 | 40 | 50 | 10 |
| 45 | 15 | 75 | 10 |
| 47 | 65 | 30 | 5 |
| 57 | 65 | 30 | 5 |

Injection vol: 10
Flow rate: 1.5 mL/min
Run time: 57 min
Detection: 245 nm

EXAMPLES

Example 1

N-(2-butyl-3-chloro-1-benzofuran-5-yl)methanesulfonamide (IIIa)

5.34 g (0.02 mol) of N-(2-butyl-1-benzofuran-5-yl)methanesulfonamide (II) is dissolved in 60 mL of dichloromethane and 60 mL of acetonitrile is added to the solution. 5.34 g (0.04 mol, 2 eq) of N-chlorosuccinimide in solid form is added dropwise at −8±2° C. in 20 min. The reaction mixture is stirred for 2 hours at this temperature and then heated up to 20° C. The reaction mixture is poured into 200 mL of water. The product is extracted with 2×80 mL of dichloromethane. The organic layer is evaporated and the residue is purified by column chromatography (spheric silica; eluent: toluene:methanol=7:3) to give 4.59 g (76%) of the title compound (IIIa) as a yellowish-brown solid.
Purity by HPLC: 99.4%.
Mp: 149-152° C.
$^1$H NMR (CDCl$_3$): 7.41 (d, J=2.2 Hz, 1H); 7.35 (d, J=8.5 Hz, 1H); 7.10 (dd, J=8.6 and 2.2 Hz, 1H); 6.71 (s, NH); 2.90 (s, 3H); 2.76 (t, J=7.2 Hz, 2H); 1.71 (m, 2H); 1.41 (m, 2H); 0.92 (t, J=7.1 Hz, 3H).

Example 2

N-(2-butyl-3-bromo-1-benzofuran-5-yl)methanesulfonamide (IIIb)

5.34 g (0.02 mol) of N-(2-butyl-1-benzofuran-5-yl)methanesulfonamide (II) is dissolved in 60 mL of dichloromethane and 5.34 g (0.03 mol, 1.5 eq) of N-bromosuccinimide in 60 mL of acetonitrile is added dropwise at −8±2° C. in 30 min. The reaction mixture is stirred for 3 hours at this temperature and then is poured into 150 mL of water. The product is extracted with 2×60 mL of dichloromethane. The organic layer is evaporated and the residue is purified by column chromatography (spheric silica; eluent: toluene:methanol=7:3) to give 4.89 g (71%) of the title compound (IIIb) as an orange solid.
Purity by HPLC: 99.1%.
Mp: 161-164° C.
$^1$H NMR (CDCl$_3$): 7.41 (d, J=2.2 Hz, 1H); 7.37 (d, J=8.5 Hz, 1H); 7.09 (dd, J=8.6 and 2.2 Hz, 1H); 6.71 (s, NH); 2.90 (s, 3H); 2.76 (t, J=7.2 Hz, 2H); 1.71 (m, 2H); 1.40 (m, 2H); 0.95 (t, J=7.1 Hz, 3H).

Example 3

N-(2-butyl-3-magnesium-chloro-1-benzofuran-5-yl) methanesulfonamide (IVa)

To a dried flask 0.92 g Mg turnings (0.04 mol) are placed and then a solution of 2.4 g of N-(2-butyl-3-chloro-1-benzofuran-5-yl)methanesulfonamide (IIIa) (0.008 mol) in 12 mL of THF is added at room temperature in 15 min. The mixture is heated slowly until the reaction starts (35-38° C.) then 9.6 g of (IIIa) (0.032 mol) in 48 mL THF is added to the reaction mixture in 40 min. During the addition the temperature of the reaction mixture reaches the reflux temperature (58-60° C.). After the addition the reaction mixture is stirred for 2 hours at reflux temperature until the solid Mg turnings disappear from the solution. The reaction mixture is cooled down to room temperature and is used in the Grignard reaction without further preparation.

Conversion by HPLC: 100%.

Example 4

N-(2-butyl-3-magnesium-bromo-1-benzofuran-5-yl) methane sulfonamide (IVb)

To a dried flask 0.92 g Mg turnings (0.04 mol) are placed and then a solution of 2.76 g of N-(2-butyl-3-bromo-1-benzofuran-5-yl)methanesulfonamide (IIIb) (0.008 mol) in 15 mL of THF is added at room temperature in 15 min. The mixture is heated slowly until the reaction starts (32-35° C.) then 11.04 g of (IIIb) (0.032 mol) in 55 mL THF is added to the reaction mixture in 45 min. During the addition the temperature of the reaction mixture reaches the reflux temperature (60-62° C.). After the addition the reaction mixture is stirred for 2 hours at reflux temperature until the solid Mg turnings disappear from the solution. The reaction mixture is cooled down to room temperature and is used in the Grignard reaction without further preparation.

Conversion by HPLC: 100%.

Example 5

4-(3-dibutylaminopropoxyl)benzamide (VIa)

6.5 g of 4-(3-dibutylaminopropoxyl)benzoyl chloride (V) (0.02 mol) is dissolved in 60 mL of n-hexane. 2.50 g of ammonium hydroxide (0.02 mol, 1 eq) and 2.76 g of potassium carbonate (0.02 mol, 1 eq) are added. The reaction mixture is heated to 50° C. and stirred for 3 hours. After the reaction the solid inorganic salt is filtered, washed with 2×5 mL of n-hexane and the filtrate is concentrated. The residue is purified by column chromatography (spheric silica; eluent: toluene:MTBE:methanol=5:4:1) to give 5.34 g of the title compound (VIa) (87%) as a yellowish solid.

Purity by HPLC: 97.9%.
M.p.: 121-123° C.
$^1$H NMR (DMSO): 7.91 (d, J=8.6 Hz, 2H); 7.7 (br, 1H); 6.86 (d, J=8.6 Hz, 2H); 4.04 (t, J=7.0 Hz, 2H); 2.56 (t, J=7.0 Hz, 2H); 2.39 (t, J=7.0 Hz, 4H); 1.87 (m, 2H); 1.33 (m, 8H); 0.86 (t, J=7.0 Hz, 6H).

Example 6

4-(3-dibutylaminopropoxy)-N,N-dimethyl-benzamide (VIb)

6.5 g of 4-(3-dibutylaminopropoxyl)benzoyl chloride (V) (0.02 mol) is dissolved in 60 mL of dichloromethane. 1.63 g of dimethylamine HCl (0.02 mol, 1 eq) is added and the reaction mixture is cooled to 0° C. 0.43 g TMSCl (0.004 mol, 0.2 eq) is added in 5 min. The reaction mixture is heated to room temperature and stirred for 5 hours. 50 mL of water is added to the mixture, it is stirred for 15 min and the phases are separated. The organic phase is washed with 30 mL of water then it is concentrated. The residue is purified by column chromatography (spheric silica; eluent: toluene:MTBE:methanol=5:4:1) to give 4.68 g of the title compound (VIb) (70%) as a yellow solid.

Purity by HPLC: 98.7%.
M.p.: 139-142° C.
$^1$H NMR (DMSO): 7.89 (d, J=8.6 Hz, 2H); 6.80 (d, J=8.5 Hz, 2H); 4.1 (t, J=7.0 Hz, 2H); 2.51 (t, J=7.0 Hz, 2H); 2.37 (t, J=7.0 Hz, 4H); 2.16 (m, 6H); 1.89 (m, 2H); 1.32 (m, 8H); 0.88 (t, J=7.0 Hz, 6H).

Example 7

4-(3-dibutylaminopropoxy)-N-methyl-N-methoxy-benzamide (VIc)

16.25 g of 4-(3-dibutylaminopropoxyl)benzoyl chloride (V) (0.05 mol) and 5.36 g of N,O-dimethyl hydroxylamine hydrochloride (0.055 mol, 1.1 eq) are dissolved in 100 mL of dichloromethane. The reaction mixture is cooled to 0° C. and 9.25 g of pyridine (0.11 mol, 2.2 eq) is added. The mixture is heated to room temperature and it is stirred for 1 hour. The solvent is evaporated in vacuum and 30 mL of brine and 30 mL of dichloromethane are added to the residue. After 15 min stirring the phases are separated and the organic phase is dried on sodium sulfate, the solvent is evaporated and the residue is purified by column chromatography (spheric silica; eluent: toluene:MTBE:methanol=5:4:1) to give 11.9 g of the title compound (VIc) (68%) as a brown solid.

Purity by HPLC: 99.3%.
M.p.: 147-148° C.
$^1$H NMR (DMSO): 7.90 (d, J=8.6 Hz, 2H); 6.86 (d, J=8.6 Hz, 2H); 4.14 (t, J=7.1 Hz, 2H); 3.86 (s, 3H); 2.71 (s, 3H); 2.56 (t, J=7.0 Hz, 2H); 2.39 (t, J=7.0 Hz, 4H); 1.87 (m, 2H); 1.33 (m, 8H); 0.86 (t, J=7.0 Hz, 6H).

Example 8

4-(3-dibutylaminopropoxy)-N,N-diethyl-benzamide (VId)

6.5 g of 4-(3-dibutylaminopropoxyl)benzoyl chloride (V) (0.02 mol) is dissolved in 60 mL of dichloromethane. 1.46 g of diethylamine (0.02 mol, 1 eq) is added and the reaction mixture is cooled to 0° C. 0.43 g TMSCl (0.004 mol, 0.2 eq) is added in 5 min. The reaction mixture is heated to room temperature and stirred for 5 hours. 50 mL of water is added to the mixture, it is stirred for 15 min and the phases are separated. The organic phase is washed with 30 mL of water then it is concentrated. The residue is purified by column chromatography (spheric silica; eluent: toluene:MTBE:methanol=5:4:1) to give 5.58 g of the title compound (VId) (77%) as a yellowish solid.

Purity by HPLC: 98.4%.
M.p.: 151-152° C.
$^1$H NMR (DMSO): 7.89 (d, J=8.6 Hz, 2H); 6.80 (d, J=8.5 Hz, 2H); 4.1 (t, J=7.0 Hz, 2H); 2.51 (t, J=7.0 Hz, 2H); 2.37 (t, J=7.0 Hz, 4H); 2.27 (m, 4H); 2.01 (m, 6H); 1.89 (m, 2H); 1.32 (m, 8H); 0.88 (t, J=7.0 Hz, 6H).

Example 9

4-(3-dibutylaminopropoxy)-N-phenyl-benzamide (VIe)

6.5 g of 4-(3-dibutylaminopropoxyl)benzoyl chloride (V) (0.02 mol) is dissolved in 60 mL of n-hexane. 1.86 g of aniline (0.02 mol, 1 eq) and 2.76 g of potassium carbonate (0.02 mol, 1 eq) are added. The reaction mixture is heated to 50° C. and stirred for 4 hours. After the reaction the solid inorganic salt is filtered, washed with 2×10 mL of n-hexane and the filtrate is concentrated. The residue is purified by column chromatography (spheric silica; eluent: toluene:MTBE:methanol=5:4: 1) to give 6.50 g of the title compound (VIe) (85%) as a yellow solid.

Purity by HPLC: 98.0%.
M.p.: 177-178° C.
$^1$H NMR (DMSO): 7.91 (d, J=8.6 Hz, 2H); 7.74 (br, 1H); 7.51 (d, 2H); 7.26 (m, 3H); 6.86 (d, J=8.6 Hz, 2H); 4.04 (t, J=7.0 Hz, 2H); 2.56 (t, J=7.0 Hz, 2H); 2.39 (t, J=7.0 Hz, 4H); 1.87 (m, 2H); 1.33 (m, 8H); 0.86 (t, J=7.0 Hz, 6H).

Example 10

N-[2-butyl-3-[4-[3-(dibutyl amino)propoxy]benzoyl]-1-benzofuran-5-yl]-methanesulfonamide (I)

6.52 g of N-(2-butyl-3-magnesium-chloro-1-benzofuran-5-yl)methanesulfonamide (IVa) (0.02 mol) in 32 mL of THF (prepared as in Example 3), 6.12 g of 4-(3-dibutylaminopropoxy)benzamide (VIa) (0.02 mol), 0.096 g of FeCl$_3$ (0.6 mmol, 0.03 eq) and 80 mL of THF are added into a flask under nitrogen. The reaction mixture is heated to 35° C. and stirred for 1 hour at this temperature. After the reaction is completed the mixture is cooled to 10° C. and poured into 1 M HCl solution, and the product is extracted with 50 mL of diethyl ether. The organic phase is washed with NaHCO$_3$ solution and evaporated. The product is purified by column chromatography (spheric silica; eluent: toluene:ethyl acetate=7:3) to give 8.80 g of dronedarone (I) (79%).

Purity by HPLC: 99.8%.
$^1$H NMR (DMSO): 7.77 (d, J=8.5 Hz, 2H); 7.27 (m, 3H); 6.91 (d, J=8.5 Hz, 2H); 5.52 (bs, 1H); 4.05 (t, J=6.0 Hz, 2H); 2.87 (s, 3H); 2.78 (t, J=7.0 Hz, 2H); 2.55 (t, J=7.0 Hz, 2H); 2.39 (t, J=7.0 Hz, 4H); 1.90 (m, 2H); 1.70 (m, 2H); 1.3-1.4 (m, 10H); 0.8-0.9 (m, 9H).

Example 11

N-[2-butyl-3-[4-[3-(dibutylamino)propoxy]benzoyl]-1-benzofuran-5-yl]-methanesulfonamide (I)

8.15 g of N-(2-butyl-3-magnesium-chloro-1-benzofuran-5-yl)methanesulfonamide (IVa) (0.025 mol) in 38 mL of THF (prepared as in Example 3), 8.36 g of 4-(3-dibutylaminopropoxy)-N,N-dimethyl-benzamide (VIb) (0.025 mol), 0.12 g of FeCl$_3$ (0.75 mmol, 0.03 eq) and 100 mL of THF are added into a flask under nitrogen. The reaction mixture is heated to 35° C. and stirred for 3 hours at this temperature. After the reaction is completed the mixture is cooled to 10° C. and poured into 1 M HCl solution, and the product is extracted with 60 mL of diethyl ether. The organic phase is washed with NaHCO$_3$ solution and evaporated. The product is purified by column chromatography (spheric silica; eluent: toluene:ethyl acetate=7:3) to give 10.44 g of dronedarone (I) (75%).

Purity by HPLC: 99.6%.
The product is identical with the compound prepared in Example 10.

Example 12

N-[2-butyl-3-[4-[3-(dibutylamino)propoxy]benzoyl]-1-benzofuran-5-yl]-methanesulfonamide (I)

9.26 g of N-(2-butyl-3-magnesium-chloro-1-benzofuran-5-yl)methanesulfonamide (IVb) (0.025 mol) in 40 mL of THF (prepared as in Example 4), 9.06 g of 4-(3-dibutylaminopropoxy)-N,N-diethyl-benzamide (VId) (0.025 mol), 0.12 g of FeCl$_3$ (0.75 mmol, 0.03 eq) and 100 mL of THF are added into a flask under nitrogen. The reaction mixture is heated to 35° C. and stirred for 3 hours at this temperature. After the reaction is completed the mixture is cooled to 10° C. and poured into 1 M HCl solution, and the product is extracted with 60 mL of diethyl ether. The organic phase is washed with NaHCO$_3$ solution and evaporated. The product is purified by column chromatography (spheric silica; eluent: toluene:ethyl acetate=7:3) to give 10.58 g of dronedarone (I) (76%).

Purity by HPLC: 99.6%.
The product is identical with the compound prepared in Example 10.

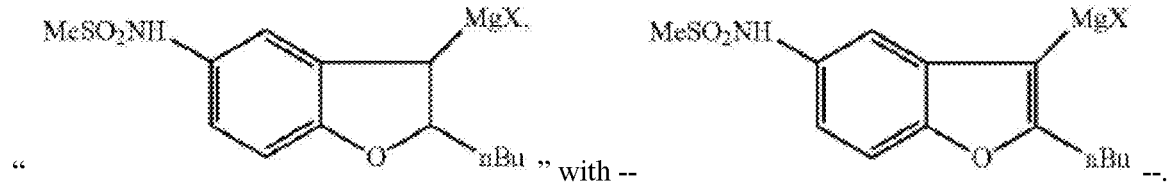

The invention claimed is:
1. A process for the preparation of dronedarone (I)

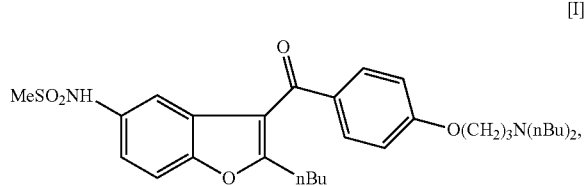

or a pharmaceutically acceptable salt thereof, comprising the steps of:
a) reacting a compound of formula (IV)

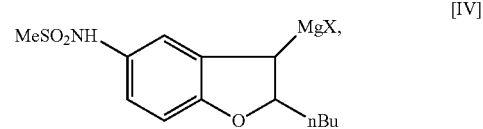

wherein X is Cl or Br, with a compound of formula (VI)

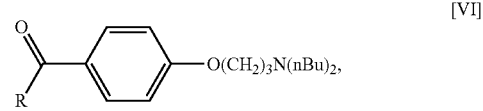

or a salt thereof, in a Grignard reaction,
wherein R is a group of formula —NR$^1$R$^2$,
wherein R$^1$ and R$^2$ are independently selected from the group consisting of H, alkyl, alkyloxy and aryl;
b) isolating dronedarone (I); and
c) optionally converting dronedarone (I) into a pharmaceutically acceptable salt thereof.
2. A compound of formula (VI),

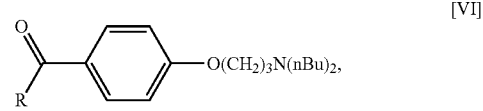

or a salt thereof, wherein R is a group of formula —NR$^1$R$^2$, wherein R$^1$ and R$^2$ are independently selected from the group consisting of H, alkyl, alkyloxy and aryl.

3. A process for the preparation of the compound of formula (VI))

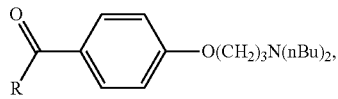

or a salt thereof,
comprising the steps of:
a) reacting a compound of formula (V)

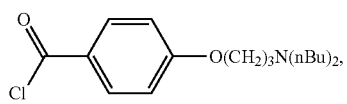

or a salt thereof, with an amine of formula H—R, or a salt thereof, in a solvent or in a mixture of solvents, wherein R is a group of formula —NR$^1$R$^2$, wherein R$^1$ and R$^2$ are independently selected from the group consisting of H, alkyl, alkyloxy and aryl;
b) isolating the compound of formula (VI); and
c) optionally converting the compound of formula (VI) into a salt thereof.

4. A compound of formula (IV)

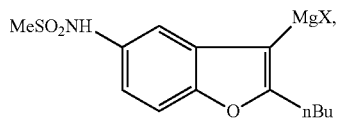

wherein X is Cl or Br.

5. A process for the preparation of the compound of formula (IV)

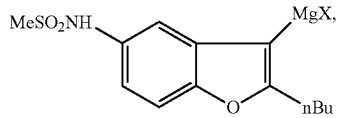

comprising reacting a compound of formula (III)

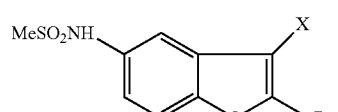

with Mg in an anhydrous solvent, wherein X is Cl or Br.

6. A compound of formula (III)

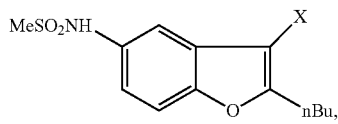

wherein X is Cl or Br.

7. A process for the preparation of the compound of formula (III)

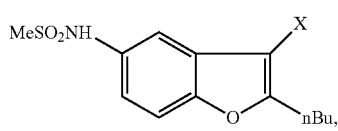

wherein X is Cl or Br,
comprising halogenating a compound of formula (II)

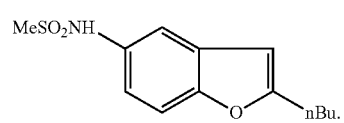

8. The process
of claim 1 further comprising a process for the preparation of the compound of formula (IV), wherein:
a compound of formula (II)

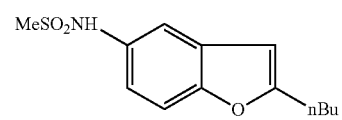

is halogenated to obtain a compound of formula (III)

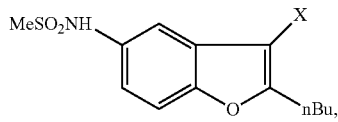

wherein X is Cl or Br; and
the obtained compound (III) is converted into the compound of formula (IV);
and further comprising a process for the preparation of the compound of formula (VI), wherein:
a compound of formula (V)

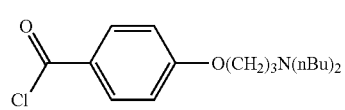

is reacted with an amine of formula H—R, wherein R is as defined in claim 1, to obtain the compound of formula (VI).

9. The process of claim 1, wherein step a) further comprises an anhydrous solvent and a catalyst.

10. The process of claim 9, wherein the solvent is THF and the catalyst is $FeCl_3$.

11. The compound of claim 2, wherein $R^1$ and $R^2$ are independently selected from the group consisting of H, methyl, ethyl, methoxy, and phenyl.

12. The process of claim 3, wherein the solvent is dichloromethane or n-hexane and wherein step a) further comprises a catalyst.

13. The process of claim 3, wherein the amine is selected from the group consisting of ammonia, dimethylamine, diethylamine, N,O-dimethyl hydroxylamine, and aniline.

14. The compound of claim 4, wherein X is Cl.

15. The compound of claim 4, wherein X is Br.

16. The compound of claim 6, wherein X is Cl.

17. The compound of claim 6, wherein X is Br.

* * * * *

UNITED STATES PATENT AND TRADEMARK OFFICE
CERTIFICATE OF CORRECTION

PATENT NO. : 9,238,636 B2
APPLICATION NO. : 14/403528
DATED : January 19, 2016
INVENTOR(S) : Csaba Huszár et al.

It is certified that error appears in the above-identified patent and that said Letters Patent is hereby corrected as shown below:

On the Title Page, Item (56):

On page 2, section "FOREIGN PATENT DOCUMENTS", left-hand side column, lines 43-44 of this section: please replace
"WO W0-03/048144 A2 6/2013
WO W0-03/048144 A3 6/2013" with
--WO WO-03/048144 A2 6/2003
WO WO-03/048144 A3 6/2003--;

On page 2, section "OTHER PUBLICATIONS", right-hand side column, line 7 of this column: please replace "ofTosylchymotrypsin" with --of Tosylchymotrypsin--;

On page 2, section "OTHER PUBLICATIONS", right-hand side column, line 11 of this column: please replace "49:45854587" with --49:4585-4587--;

On page 2, section "OTHER PUBLICATIONS", right-hand side column, line 12 of this column: please replace "a,6-Alkynylketones" with --α,β-Alkynylketones--;

On page 2, section "OTHER PUBLICATIONS", right-hand side column, line 14 of this column: please replace "32(48):70917092" with --32(48):7091-7092--;

On page 2, section "OTHER PUBLICATIONS", right-hand side column, line 57 of this column: please replace "Desmethyiated" with --Desmethylated--;

Signed and Sealed this
Fifth Day of July, 2016

Michelle K. Lee
*Director of the United States Patent and Trademark Office*

CERTIFICATE OF CORRECTION (continued)

On page 2, section "OTHER PUBLICATIONS", right-hand side column, line 64 of this column: please replace "lnitio" with --Initio--;

On page 2, section "OTHER PUBLICATIONS", right-hand side column, line 71 of this column: please replace "6-Diketones" with --β-Diketones--;

On page 2, section "OTHER PUBLICATIONS", right-hand side column, line 72 of this column: please replace "c-Acylcaproic" with --ε-Acylcaproic--;

On page 3, section "OTHER PUBLICATIONS", left-hand side column, line 18 of this section: please replace "6-Ketoamines" with --β-Ketoamines--;

On page 3, section "OTHER PUBLICATIONS", left-hand side column, line 24 of this section: please replace "El Sevior" with --Elsevier--;

On page 3, section "OTHER PUBLICATIONS", left-hand side column, line 38 of this section: please replace "0-(nitrofenil)-acetofenonoxime" with --O-(nitrofenil)-acetofenonoxime--;

On page 3, section "OTHER PUBLICATIONS", left-hand side column, line 40 of this section: please replace "0-Arilarea" with --O-Arilarea--;

On page 3, section "OTHER PUBLICATIONS", left-hand side column, line 45 of this section: please replace "Wiley lnterscience" with --Wiley Interscience--;

On page 3, section "OTHER PUBLICATIONS", left-hand side column, line 48 of this section: please replace "Wiley lnterscience" with --Wiley Interscience--;

On page 3, section "OTHER PUBLICATIONS", left-hand side column, lines 53-54 of this section: please replace "a-Dialkylamino-w-Methylaminoalkanes" with --α-Dialkylamino-ω-Methylaminoalkanes--;

On page 3, section "OTHER PUBLICATIONS", left-hand side column, line 58 of this column: please replace "20-Hydroxy5,6,11,14-Eicosatetraenoic" with --20-Hydroxy-5,6,11,14-Eicosatetraenoic--;

On page 3, section "OTHER PUBLICATIONS", right-hand side column, line 13 of this column: please replace "Acs" with --ACS--;

On page 3, section "OTHER PUBLICATIONS", right-hand side column, line 18 of this section: please replace "Iodoacetic" with --Iodoacetic--;

On page 3, section "OTHER PUBLICATIONS", right-hand side column, line 19 of this section: please replace "L-Methionine to L-Homoserine" with --$_L$-Methionine to $_L$-Homoserine--;

On page 3, section "OTHER PUBLICATIONS", right-hand side column, lines 20-21 of this section: please replace "11 1(4): 1363-1367." with --111(4):1363-1367.--; and On page 3, section "OTHER PUBLICATIONS", right-hand side column, line 42 of this section: please replace "61:78337863" with --61:7833-7863--.

In the Claims:

At column 12, claim number 1, line number 35: please replace